(12) United States Patent
Funakoshi et al.

(10) Patent No.: US 8,209,135 B2
(45) Date of Patent: Jun. 26, 2012

(54) WAFER INSPECTION DATA HANDLING AND DEFECT REVIEW TOOL

(75) Inventors: Tomohiro Funakoshi, Hitachinaka (JP); Junko Konishi, Yokohama (JP); Yuko Kariya, Hitachinaka (JP); Noritsugu Takahashi, Kokubunji (JP); Fumiaki Endo, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/040,794

(22) Filed: Mar. 4, 2011

(65) Prior Publication Data

US 2011/0211060 A1 Sep. 1, 2011

Related U.S. Application Data

(63) Continuation of application No. 11/594,757, filed on Nov. 9, 2006, now abandoned.

(30) Foreign Application Priority Data

Nov. 10, 2005 (JP) .................................. 2005-326123

(51) Int. Cl.
  *H04N 7/18* (2006.01)
(52) U.S. Cl. ................ 702/35; 702/33; 702/34; 702/36; 382/145; 382/149; 382/155; 382/159; 382/299; 250/306; 250/307; 250/310; 348/80; 348/125; 348/126
(58) Field of Classification Search .............. 702/33–36; 382/145, 149, 155, 159, 299; 348/125–126, 348/80; 250/306, 307, 310
See application file for complete search history.

(56) References Cited

U.S. PATENT DOCUMENTS

| | | | |
|---|---|---|---|
| 6,259,960 | B1 | 7/2001 | Inokuchi |
| 6,292,582 | B1 | 9/2001 | Lin et al. |
| 6,411,377 | B1 | 6/2002 | Noguchi et al. |
| 6,657,221 | B2 | 12/2003 | Nakagaki et al. |
| 6,797,975 | B2 | 9/2004 | Nishiyama et al. |
| 6,888,959 | B2 | 5/2005 | Hamamatsu et al. |
| 6,959,251 | B2 | 10/2005 | Coldren et al. |
| 7,072,786 | B2 | 7/2006 | Coldren et al. |
| 7,508,973 | B2 | 3/2009 | Okabe et al. |
| 2003/0050761 | A1* | 3/2003 | Okabe et al. .................... 702/82 |

FOREIGN PATENT DOCUMENTS

| | | |
|---|---|---|
| JP | 07-074787 | 8/1995 |
| JP | 10-135288 A | 5/1998 |
| JP | 2000-233345 A | 2/2000 |

(Continued)

OTHER PUBLICATIONS

Japanese Office Action issued in Japanese Patent Application No. 2005-326123, mailed Jan. 5, 2010.

(Continued)

*Primary Examiner* — Sujoy Kundu
(74) *Attorney, Agent, or Firm* — McDermott Will & Emery LLP (57) ABSTRACT

A defect detected by a wafer inspection tool is reliably captured by a defect review tool. A defect review condition in the defect review tool is varied depending on defect attributes provided by the wafer inspection tool so as to optimize the review process. For example, review magnification is varied depending on the size of the defect, or the frame addition number is varied depending on the maximum gray level difference.

10 Claims, 7 Drawing Sheets

FOREIGN PATENT DOCUMENTS

| | | |
|---|---|---|
| JP | 2001-156141 A | 6/2001 |
| JP | 2001-250852 | 9/2001 |
| JP | 2002-310962 | 10/2002 |
| JP | 2003-098111 | 4/2003 |
| JP | 2004-134758 A | 4/2004 |
| JP | 2005-017159 | 1/2005 |

OTHER PUBLICATIONS

Entire Prosecution of U.S. Appl. No. 11/594,757 to Funakoshi, et al., filed on Nov. 9, 2006, entitled "Wafer Inspection Data Handling and Defect Review Tool".

* cited by examiner

Lot No. : _______
Wafer ID : _______
Die Layout : _________

| Defect ID | x Coordinate | y Coordinate | Maximum Gray Level Difference | Defect Size |
|---|---|---|---|---|
| 1 | x1 | y1 | d1 | s1 |
| 2 | x2 | y2 | d2 | s2 |
| 3 | x3 | y3 | d3 | s3 |

FIG. 4

RDC Parameter Table

Maximum Gray Level Difference
Reference Image Average Gray Level
Defect Image Average Gray Level
Polarity
Inspection Mode
Defect Size
Defect Pixel Number
Defect Size Width
Defect Size Height
Defect Size Ratio (width/height)
Defect-Pixel Differential Value on Defect Image
Defect-Pixel Differential Value on Reference Image

Lot No. : _______
Wafer ID : _______
Die Layout : _________

| Defect ID | x Coordinate | y Coordinate | Maximum Gray Level Difference | Defect Size |
|---|---|---|---|---|
| 1 | x1 | y1 | d1 | s1 |
| 2 | x2 | y2 | d2 | s2 |
| 3 | x3 | y3 | d3 | s3 |

WAFER INSPECTION DATA HANDLING AND DEFECT REVIEW TOOL

RELATED APPLICATIONS

The present application is a Continuation of U.S. patent application Ser. No. 11/594,757, filed Nov. 9, 2006, Now Abandoned and claims priority from Japanese application JP 2005-326123 filed on Nov. 10, 2005, the entire contents of each of which are hereby incorporated by reference into this application.

BACKGROUND OF THE INVENTION

1. Field of the Invention

The invention relates to a defect review operation concerning products or components being manufactured. Particularly, the invention relates to a system for improving the efficiency of the process of determining conditions in a tool for detecting particles or pattern defects on the surface of a semiconductor wafer, photo mask, magnetic disc, or liquid crystal display substrate, for example.

2. Background Art

In semiconductor production, particles or pattern defects on the surface of a wafer during the production process may lead to defective products. Therefore, it is necessary to quantify such particles or pattern defects (to be hereafter referred to as defects) and constantly monitor the manufacturing equipment or environment for possible problems. It is also necessary to observe the shape of such a defect so as to determine if it could have a fatal impact on the final product.

Conventionally, such observation of shapes has often been conducted manually by an operator. This has resulted in problems such as the presence of a bias in the position of a defect in the observed object depending on the operator, or the lack of uniformity in the defects to be observed. In order to solve these problems, technologies are being introduced such as automatic defect review (ADR) and automatic defect classification (ADC). For example, a system has been proposed for reducing the burden on the operator and facilitating an efficient operation when observing or reviewing a part (such as a pattern formed on a wafer) that has been inspected by a wafer inspection tool using an SEM (Scanning Electron Microscopy) defect review tool (see JP Patent Publication (Kokai) No. 10-135288 A, for example). A means has also been proposed for arranging the enormous amount of information including the defect ID (identification number) and coordinates information provided by the wafer inspection tool and the ADR and ADC information provided by the defect review tool, thereby facilitating defect analysis (see JP Patent Publication (Kokai) No. 2001-156141 A, for example). According to this proposal, the information provided by the wafer inspection tool consists of the name of product and wafer identification numbers, such as the lot number and wafer number, the name of the process step under investigation, and the coordinates information about a detected defect, for example.

Patent Document 1: JP Patent Publication (Kokai) No. 10-135288 A

Patent Document 2: JP Patent Publication (Kokai) No. 2001-156141 A

SUMMARY OF THE INVENTION

In response to the shrinkage in defect size, the modern inspection of the state-of-the-art devices may involve assigning a plurality of inspection conditions and obtaining a single result as an output. Further, as a result of the increase in the sensitivity of wafer inspection tools, the influence of noise has also increased, resulting in the total number of defects that are detected sometimes exceeding several tens of thousands or more. In order to eliminate such noise, a technique is employed whereby defects are classified by the RDC (Real-Time Defect Classification) function on the wafer inspection tool during inspection. However, in order to determine the defect detection condition and the RDC condition for the elimination of noise accurately on the part of the wafer inspection tool, it is necessary to collate as much information provided by the wafer inspection tool with as much information provided by the defect review tool (observing device) as possible.

As mentioned above, the operation for detecting defects is very important for achieving higher yields. On the other hand, as semiconductor devices shrink in size, wafer inspection tools are being required to provide better capability and performance for defect detection. Wafer inspection tools have actually appeared that are capable of detecting defects with higher sensitivity. Such enhanced sensitivity has also enabled the detection of very small defects, resulting in very large numbers of defects that are detected in which increasingly noise is also detected. This has led to a very large number of defects whose shapes need to be confirmed using a defect review tool in a review operation. It has also led to an increase in the number of cases where no defects can be found by the review operation, resulting in a decrease in operational efficiency. In addition, there has been an explosive increase in the volume of information that needs to be fed back for the purpose of inspection and RDC condition determination in order to reduce such noise, making it ever more difficult to determine inspection conditions accurately.

Because the conventional operation of collating the information from the wafer inspection tool with the information from the defect review tool is often done manually by the operator, the collating method may vary from one operator to another, or variations could be introduced in the inspection conditions finalized in accordance with the result of such collation. It has also been difficult to set sensitivity to such a level that no noise that does not need to be detected in actual defect detection would be detected.

Even if the inspection conditions can be optimized, defects that can be detected become smaller and smaller as the wafer inspection tool achieves higher sensitivity, resulting in a need for a high-performance defect review tool for identifying such defects. However, defects having low signal levels upon defect detection are so small that their review is difficult. Thus, there are many defects of which identification is difficult and which cause a decrease in yield. It is becoming increasingly difficult to review such defects and to distinguish noise from defects accurately.

It is therefore an object of the invention to achieve higher efficiency in defect extraction while reducing the time it takes for the determination of an inspection condition that is set in a wafer inspection tool for detecting defects. For this purpose, the invention allows a defect detected by a wafer inspection tool to be captured by a defect review tool reliably.

In accordance with the invention, a review image in which a defect is reliably captured is easily obtained as information guiding the determination of such a defect inspection condition that a DOI (Defect of Interest) can be detected while reducing noise and improving the average defect capture ratio. For this purpose, the defect review condition in the defect review tool is varied depending on the defect attributes provided by the wafer inspection tool so as to optimize the reviewing process.

Specifically, based on a setting such that RDC attributes can be outputted by the wafer inspection tool, a data handling tool is prepared that is connected to both the wafer inspection tool and the defect review tool via a network. The data handling tool processes the data provided by the wafer inspection tool and the defect review tool, and causes the defect ID of the result of inspection, which is performed a plurality of times with the same or varying inspection condition, a corresponding image data, and RDC attributes to be displayed and arranged. Data concerning the same defect is grouped by collating the coordinates, and such defect information (coordinates and attributes) is outputted to the defect review tool. Based on the information, the defect review tool modifies the review condition either manually or automatically, and acquires an image using such a review condition under which even a defect that is particularly difficult to observe can be captured in the image. The thus obtained image is then fed back to the data handling tool and displayed alongside the information provided by the wafer inspection tool. The data handling tool may be integrally constructed with the defect review tool.

In accordance with the invention, defect attributes, such as the signal level of a defect, for example, are outputted to the defect review tool, and the review conditions of the defect review tool are optimized on the basis of that information. This allows the capture of an image of a very small defect that has been heretofore difficult to obtain. The image is then displayed alongside the information outputted by the wafer inspection tool, whereby the time it takes for the optimization of the inspection conditions for DOI detection can be reduced.

DESCRIPTION OF THE PREFERRED EMBODIMENT OF THE INVENTION

In the following, an embodiment of the invention will be described with reference to the drawings, where the invention is applied to a semiconductor production line.

Figure 1:
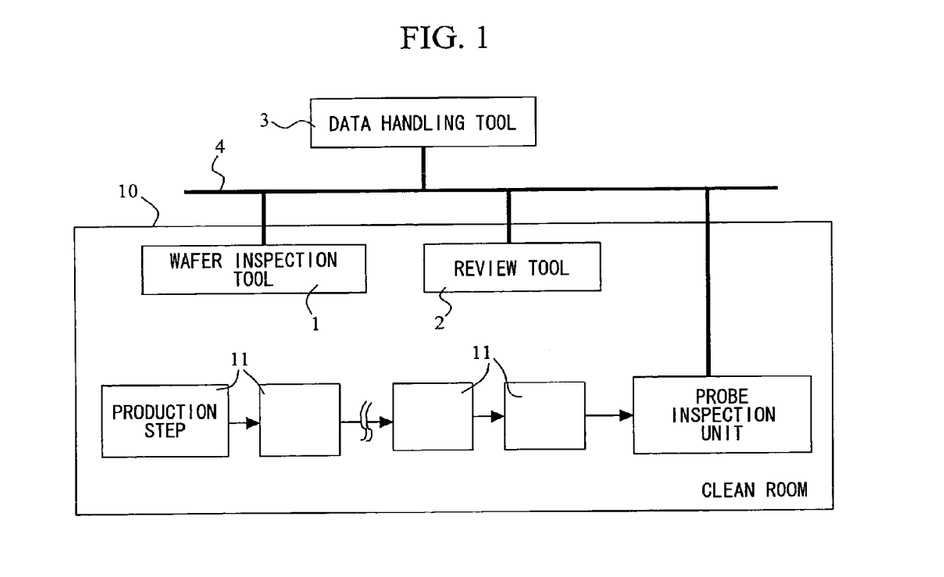
FIG. 1 shows an overall structure of a defect review assist system including a data handling tool according to the invention.
Figure 2:
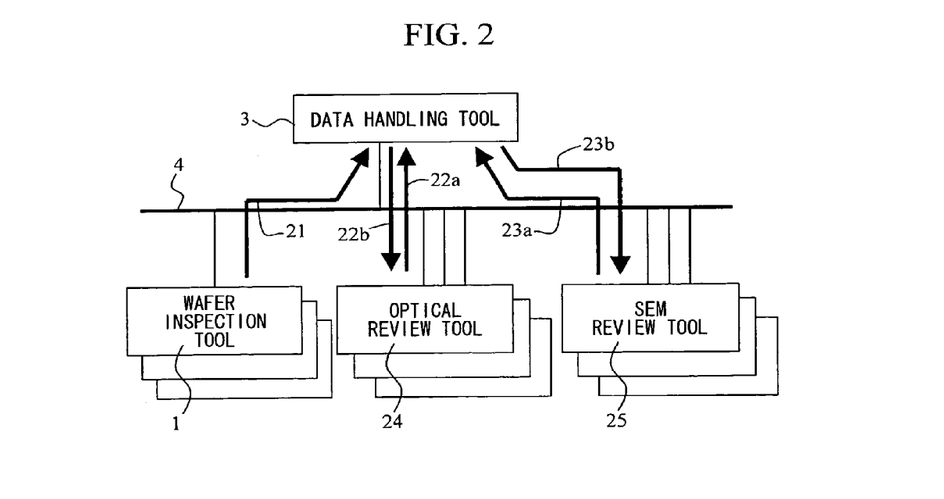
FIG. 2 shows how information is exchanged between various units.
Figure 3:
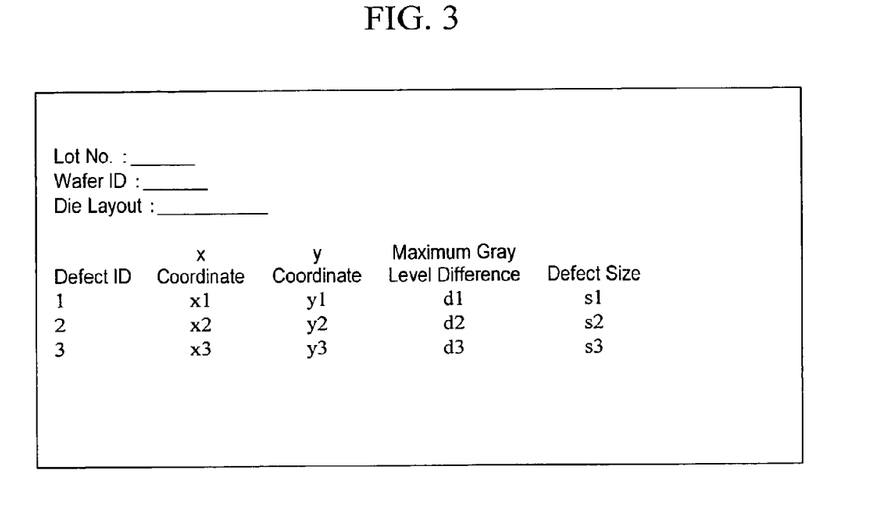
FIG. 3 shows an example of defect information exchanged between a wafer inspection tool and a defect review tool.

An example of the defect review assist system of the invention will be described with reference to FIGS. 1, 2, and 3. FIG. 1 shows an example of the overall structure of the system. FIG. 2 shows how the defect attributes and ADR image information provided by the wafer inspection tool and the ADR/ADC information provided by the defect review tool are exchanged. FIG. 3 shows an example of the defect information exchanged between the wafer inspection tool and the defect review tool. While in the example shown in FIGS. 1 and 2 the data handling tool is shown independently provided, alternatively the data handling tool may be integrally constructed with the wafer inspection tool or the defect review tool.

Semiconductor production steps 11 are normally implemented in a clean room 10 in which a clean environment is maintained. The clean room 10 houses a wafer inspection tool 1 for detecting a defect in a product wafer, and a defect review tool 2 for reviewing, i.e., observing the defect based on the data provided by the wafer inspection tool 1. The wafer inspection tool 1 and the defect review tool 2 are connected with a data handling tool 3 for the exchange of inspection/image data, via a communications line 4. The product wafers flow through the semiconductor production steps 11 on a lot-unit basis. Wafer inspection is performed after the completion of the production step that requires wafer inspection, at the wafer inspection tool 1 to which the wafer is transferred by the operator or a transferring robot. After the wafers are processed through the production steps 11 and by the wafer inspection tool 1 and the defect review tool 2, each chip on the wafer is finally checked by a probe machine to make sure that there is no problem in its electric characteristics.

Defect information 21 obtained by wafer inspection is managed by the data handling tool 3 with respect to the lot number, wafer number, inspection step, and date of inspection. FIG. 3 shows an example of the defect information 21, which consists of the lot number, wafer ID, die layout, defect ID of a defect that has been detected during inspection, and its coordinate information, for example. The defect information 21 may also contain a defect ADR image, defect attributes information (RDC information), and so on.

Figure 4:
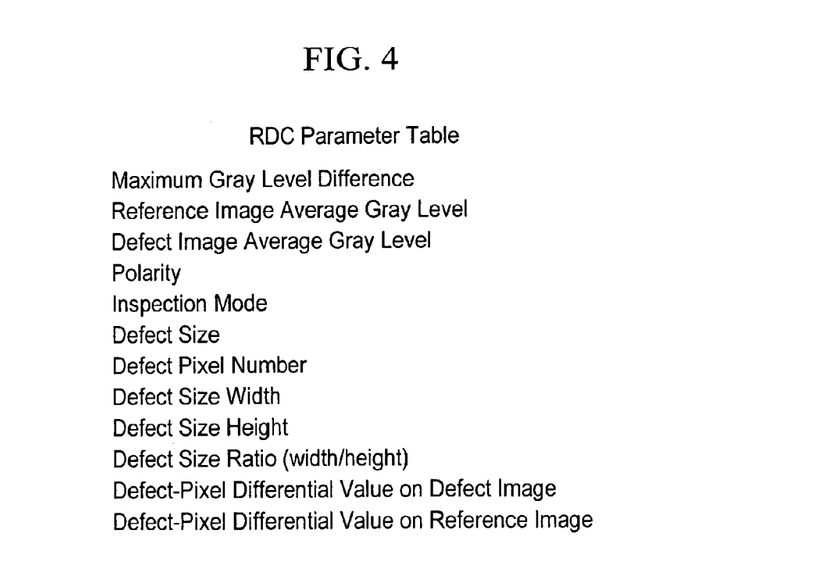
FIG. 4 shows an example of the screen on which defect attributes provided by the wafer inspection tool are shown.

An example of defect attributes information is shown in FIG. 4. This data is transmitted in the form of text data in a predetermined format, together with other defect information. Conventionally, the defect information provided by the wafer inspection tool has consisted only of defect ID, its coordinates, and size, for example.

In order to optimize the inspection sensitivity of this wafer inspection, it is conventional to repeat inspection a plurality of times while varying threshold conditions and optical conditions such as focus offset and inspection magnification. As the inspection conditions are optimized during such multiple inspections, more and more DOIs may be detected, making it increasingly difficult to not only detect but also review them. As a result, there have been cases where, even though a DOI is detected, the review provides nuisance, i.e., it concludes that no defect image has been found, thus introducing an error in the setting of optimum inspection conditions. In accordance with the invention, such erroneous judgment is prevented by making the review conditions in the defect review tool variable using the defect attributes information provided by the wafer inspection tool. Thus, the invention provides a means for determining optimum inspection conditions in the wafer inspection tool based on the result of a plurality of inspections.

Hereafter the parameters shown by way of example in FIG. 4 are described. The maximum gray level difference refers to the absolute value of the gray level of a defect portion in a subtract image, which is obtained by processing the image of a location determined to include a defect and a corresponding reference image. The reference image average gray level refers to an average value of the gray levels of a pixel portion on the reference image that has been determined to be the defect portion. The defect image average gray level refers to an average value of the gray levels of a pixel portion on the defect image that has been determined to be the defect portion. The polarity indicates whether the defect portion is brighter or darker than the reference image: "+" designates a brighter defect, and "−" designates a darker defect. The inspection mode refers to the image comparison method used when a particular defect was found. It includes the die-to-die method, the cell-to-cell method, and their hybrid method. The defect size, defect pixel number, and the width/height ratio of the defect show the size of the detected defect, where the defect size and the width/height ratio are in units of micrometers and the defect pixel number is in units of pixels. The defect size ratio is a parameter representing the width-to-height ratio of the defect size. If the width and height were the same, the parameter would be 1; if the width were twice the height, the parameter would be 2, and so on. The defect pixel differential value represents a differential value of the pixel portion on the defect image or the reference image that has been determined to be a defect. The value indicates the rate of change of gray value in the pixel portion. The value in the defect image portion is referred to as a defect-pixel differential value on defect image, while the corresponding value in the reference image portion is referred to as a defect-pixel differential value on reference image.

The wafer of which wafer inspection has been completed is transferred to the defect review tool 2 for defect review. Specifically, a predetermined wafer is picked out of the lot and reviewed. Upon review, defect information 22b and 23b is acquired from the data handling tool 3, using the information about the wafer to be reviewed. i.e., the lot number, wafer number, and inspection step, as key information. The defect information includes not only the defect ID and coordinates data but also defect attributes obtained upon inspection. Conventionally, the defect information 22b and 23b has not included the defect attributes provided by the wafer inspection tool.

Because the defect information 21 provided by the wafer inspection tool 1 consists of a huge volume of data, the defect information 22b or 23b, which is extracted by the data handling tool 3 using multiple filter functions, is sent to the optical defect review tool 24 or an SEM defect review tool 25 via the communications line 4. The defect information 22b and 23b is generally in the same format as the defect information 21.

Based on the extracted defect information 22b or 23b, the optical defect review tool 24 or SEM defect review tool 25 acquires an image of the defect detected portion. Defect classification is then carried out based on the image by the ADC function installed on each defect review tool. Specifically, the wafer of which wafer inspection has been completed is retained on the sample stage of the optical defect review tool 24 or SEM defect review tool 25. The stage is moved to the coordinates position of the defect contained in the defect information 22b or 23b, where a defect image is acquired. The defect is then classified according to the features of the thus acquired defect image. The resultant information is sent to the data handling tool 3 as ADR/ADC information 22a or 23a via the communications line 4.

Figure 5:
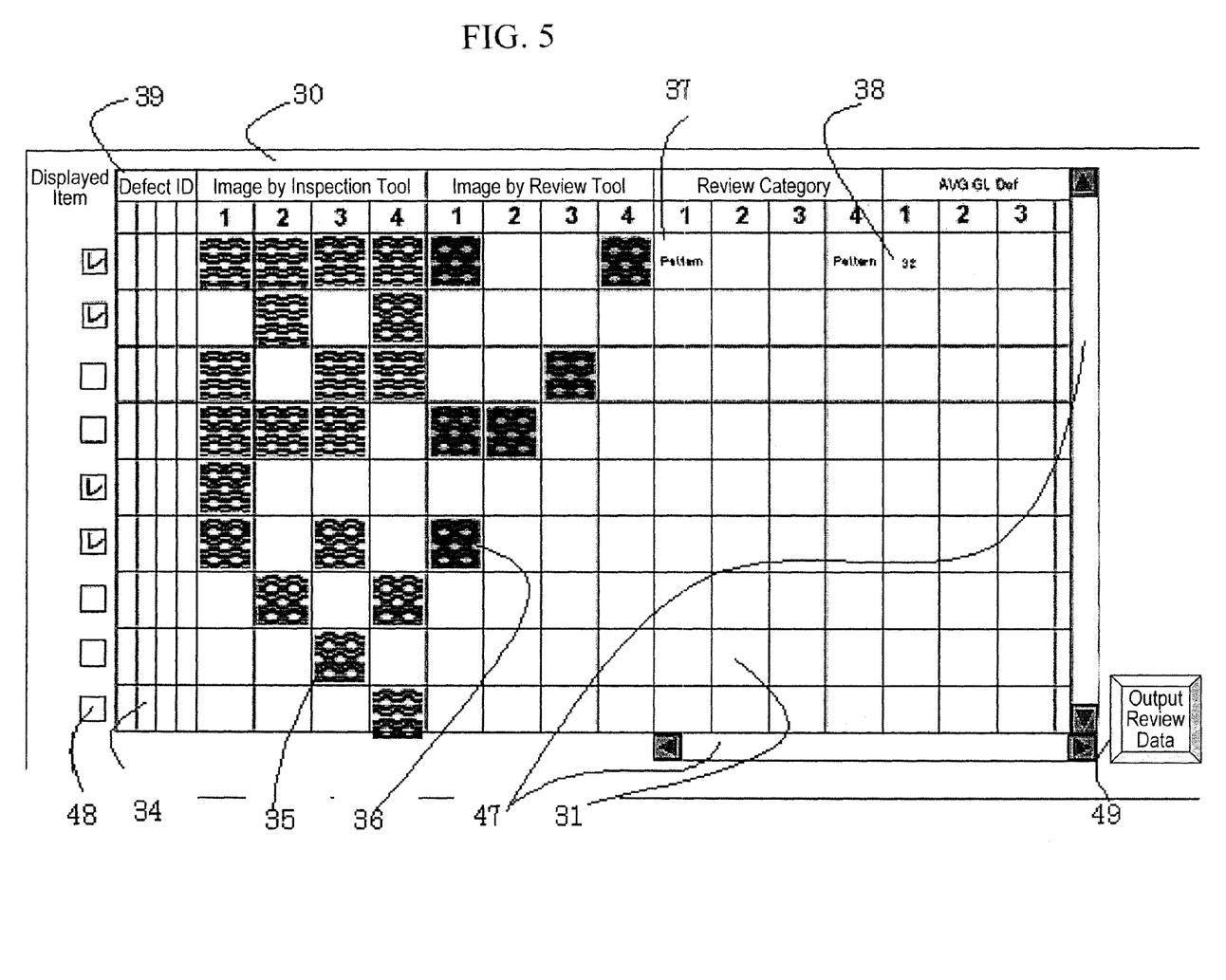
FIG. 5 shows an example of the screen displayed on the data handling tool.

With reference to FIG. 5, it is described in the following how the inspection defect attributes and image data provided by the wafer inspection tool and the ADR/ADC information provided by the defect review tool are displayed and processed by the data handling tool according to the invention.

The large volume of inspection/image data provided by the wafer inspection tool, and also the large volume of ADR/ADC information provided by the defect review tool are displayed side by side. For this purpose, a screen 30 shown in FIG. 5 is prepared on the data handling tool.

The screen 30 includes a table 31 showing the defect ID 34 and ADR image 35 provided by the wafer inspection tool, the defect attributes 38, and the ADR image 36 and ADC classification information 37 provided by the defect review tool, each under a heading 39. Any location of the table can be designated using scroll bars 47. The screen 30 also includes buttons 48 for directly selecting the defect information to be displayed. The headings 39 show the defect ID, image by wafer inspection tool, image by defect review tool, review category, and the maximum gray level difference, which are the parameters shown in FIG. 4 indicating defect attributes. Concerning those defects that are determined to be identical and have the same coordinates based on a collation of the coordinates of the defects that have been detected in a plurality of inspections with the same or varying inspection conditions, the table 31 shows the information about such defects on the same line. The table shown concerns an example in which inspection was conducted four times with the same inspection conditions or with varying inspection conditions in terms of focus offset, inspection threshold, and inspection magnification, for example, so that a maximum of four kinds of information are shown for a single defect. For example, with regard to the defect shown at the top in FIG. 5, four images from the wafer inspection tool are displayed. As to the ADR image 35 from the wafer inspection tool and the ADR image 36 from the defect review tool, the corresponding columns are empty if there is no such images for a particular defect ID. A button 49 is provided for outputting the result of coordinates collation and the defect attributes 38 in the format of FIG. 3. As a means for displaying a desired location, the screen includes the scroll bars 47.

By clicking any of the headings 39, the information contained in the table can be sorted in the ascending or descending order based on the information about the heading clicked. For example, by clicking AVG GL Def, 1, the entire information is sorted in the ascending or descending order of the AVG GL Def. Such sorting allows for an easy understanding of what kind of defect has what attributes. Furthermore, by referring to the defect pictured in the image provided by the wafer inspection tool or the defect review tool, it can be easily confirmed what appearance the defect of real concern should have, and whether or not it is a nuisance defect. In the example of table 31, information about each defect ID is displayed side by side horizontally; it goes without saying, however, that the same information may be arranged vertically.

With reference now to FIGS. 2, 3, and 6-8, the function of the review data creating button 49 included in the screen 30 of FIG. 5, and the defect review method of the invention, which is implemented by the defect review tool using that function are described. It should be obvious that the following descriptions do not limit the invention.

Figure 6:
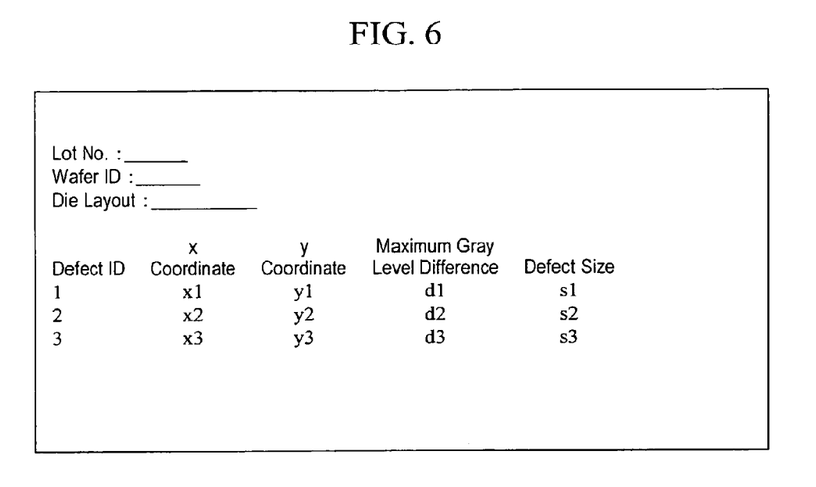
FIG. 6 shows an example of the defect information outputted by the data handling tool to the defect review tool.

First, on the screen 30 shown in FIG. 5, the results of a plurality of inspections that need to be subjected to data processing are displayed. As the review data creating button 49 is depressed, review data is created (22b and 23b of FIG. 2) as shown in FIG. 6. Such review data includes the defect ID, defect size, and attributes that have been displayed on the screen 30 of FIG. 5 when depressing the review data creating button 49. This review data is sent to the optical defect review tool 24 or the SEM defect review tool 25 of FIG. 2 via the network 4 of FIG. 2.

Figure 7:
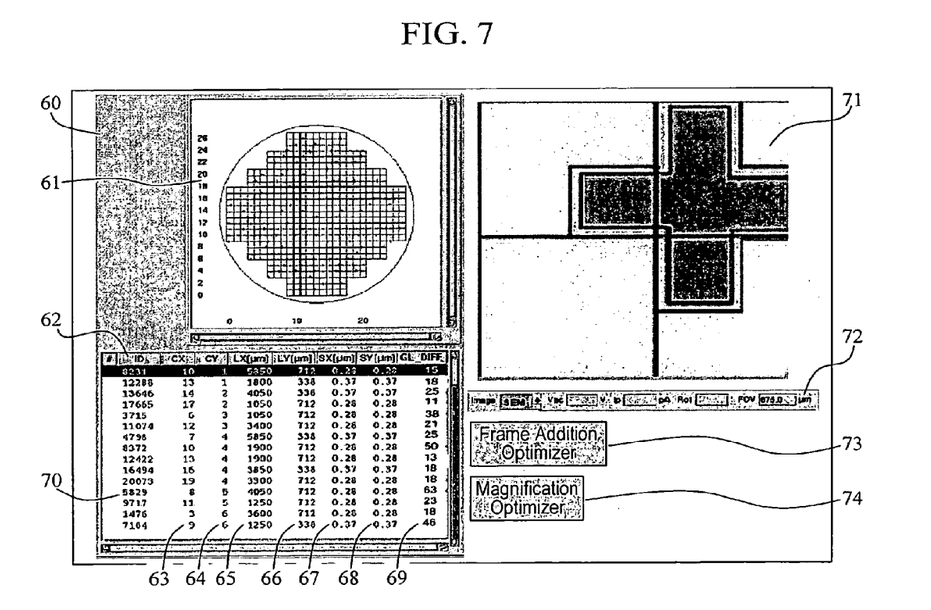
FIG. 7 shows an example of the operation screen of the defect review tool.

FIG. 7 shows an operation screen 60 of the optical defect review tool 24 or the SEM defect review tool 25. This screen shows a defect map 61 showing the distribution of defects as dots on a wafer map, based on the information 22b and 23b acquired from the wafer inspection tool. The screen also shows a defect list 70 showing IDs 62 of the defects shown on the defect map, the X coordinate 63 of the die, Y coordinate 64 of the die, intra-die X coordinate 65, intra-die Y coordinate 66, X-direction size 67 of the defect, Y-direction size 68 of the defect, and the defect maximum gray level difference 69, for example. In addition, the screen shows a defect review image 71, a defect review condition table 72, a frame addition optimizer button 73, and a magnification optimizer button 74. By clicking a desired point on the map 61 indicating a defect, or any given defect information in the list 70, any defect that is to be reviewed can be shown in the defect review image 71.

In conventional defect review tools, the information provided by the wafer inspection tool has consisted only of the defect ID, coordinates, and size. As a result, regardless of the features of a given defect, a defect image has been acquired merely with the same electron beam acceleration voltage, probe current, and frame addition number under the same review conditions in, for example, the SEM defect review tool.

Figure 8:
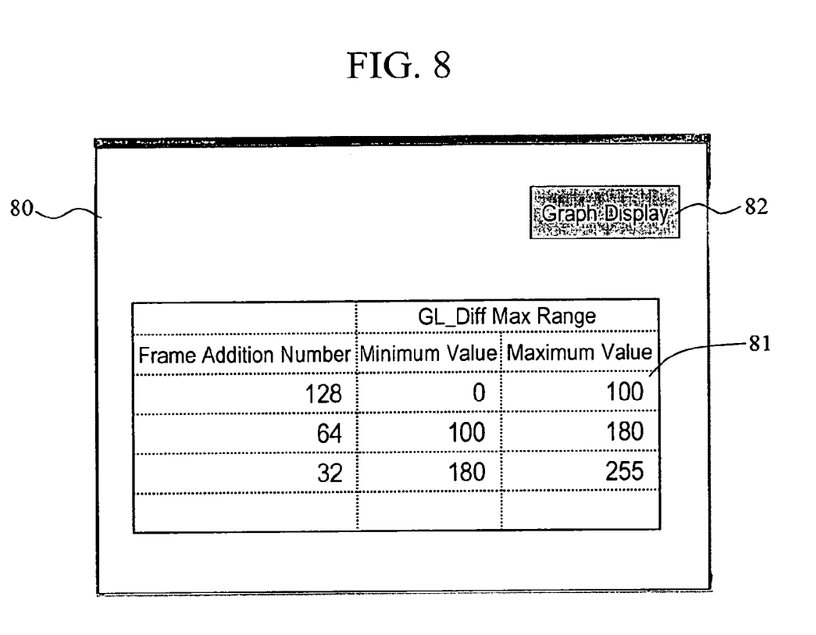
FIG. 8 shows an example of a frame addition optimizer window.
Figure 10:
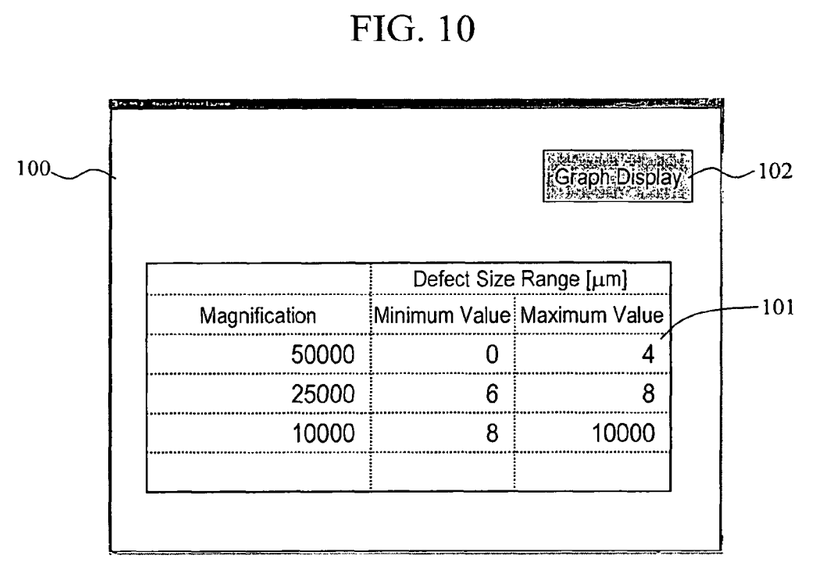
FIG. 10 shows an example of a magnification optimizer window.

In accordance with the invention, using a window 80 shown in FIG. 8 that appears upon pressing the frame addition optimizer button 73 on the operation screen 60, or by using a window 100 shown in FIG. 10 that appears upon pressing of the magnification optimizer button 74, the frame addition number or the magnification of the defect to be reviewed can be varied depending on the maximum gray level difference or the size of the subtract image upon detection by the wafer inspection tool. In this way, the invention aims to make it possible to reliably capture an image of even those defects having a small maximum gray level difference, i.e., defects that have been difficult to detect using the wafer inspection tool and of which review by the defect review tool has also been difficult.

Figure 9:
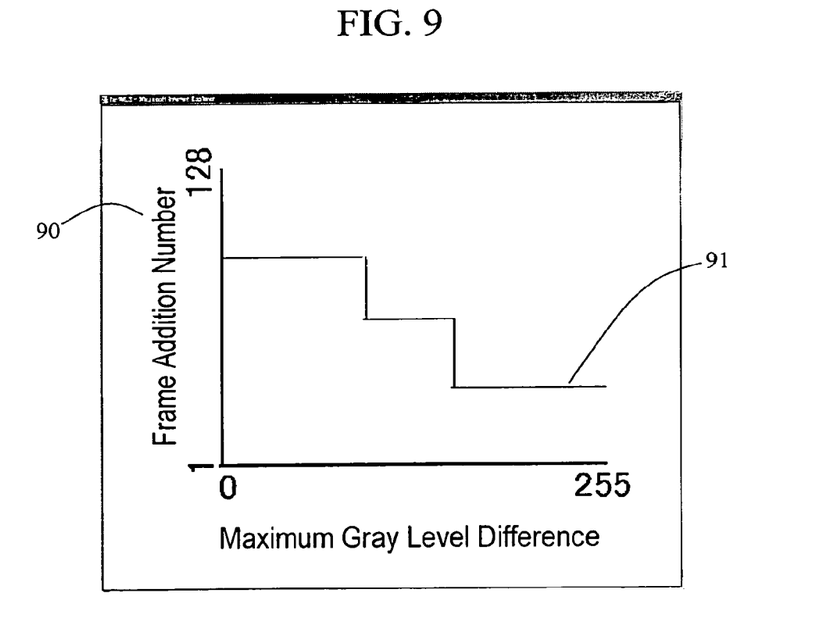
FIG. 9 shows an example of a graph window for the confirmation of the setting of the frame addition optimizer.

The window 80 of FIG. 8 that appears upon pressing of the button 73 shows a table 81 for the setting of a frame addition number and for the setting of a range of maximum gray level difference (Max GL_Diff) for the application of that value, and a graph button 82 for the confirmation of those settings on a graph. Upon clicking of the button 82, a graph 90 is displayed in which the gray level difference is shown on the horizontal axis and the number of image addition frames is shown on the vertical axis. Use of these tables makes it possible to make settings such as shown in FIG. 8, for example, where the frame addition number of 128 is allocated to the gray level difference of 100 or less, 64 to the difference of 100 or more and 180 or less, and 32 to 180 or more. In this way, it becomes possible to obtain a defect image having lower noise levels and better image quality by increasing the frame addition for those defects with small signal levels. Thus, the number of cases where determination of noise is difficult can be reduced. Also, the number of cases where, after a defect image is acquired by the defect review tool, the wafer has to be transferred to the defect review tool for a repeated review due to failure to make a determination can be dramatically reduced. While the values in the table 81 displayed in the window 80 of FIG. 8 are default values determined through experience or otherwise, the user may alternatively modify them as needed.

Figure 11:
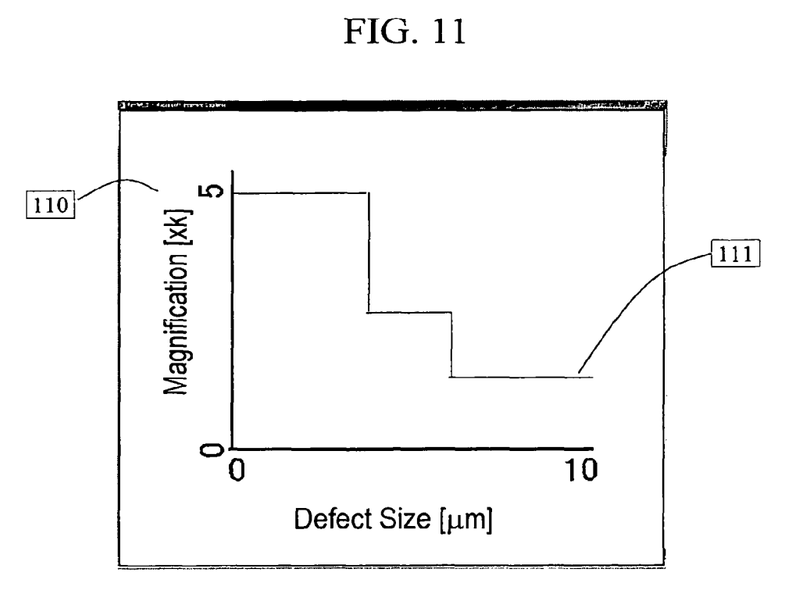
FIG. 11 shows an example of a graph window for the confirmation of the setting of the magnification optimizer.

The window 100 of FIG. 10 that appears upon pressing of the button 74 shows a table 101 for the setting of magnification and a range of defect size in which the relevant value should be applied, and a graph button 102 for the confirmation of those settings on a graph. Upon clicking of the button 102, a graph 110 is displayed in which the defect size is shown on the horizontal axis and the magnification on the vertical axis. Using those settings, it becomes possible to obtain an image with magnification of ×50,000 for defect size of 4 µm or less, ×25,000 for defect size of 4 µm or more and 6 µm or less, and ×10,000 for greater sizes, as shown in FIG. 10, for example. Because lower magnification can be used for larger defects, it also becomes possible to reliably capture an overall image of a large defect. While the values in the table 101 displayed in the window 100 of FIG. 10 are default values that are determined in advance through experience or otherwise, the user may alternatively modify those values as needed.

While the foregoing examples of graphs displayed in the windows 90 and 110 were line graphs 91 and 111, other forms of graph may be employed, such as a bar graph, a radar chart, and so on.

Thus, by modifying the review conditions such as the frame addition number and magnification depending on the attributes of the defect to be reviewed, an image of a defect can be reliably obtained in the defect review tool.

Figure 12:
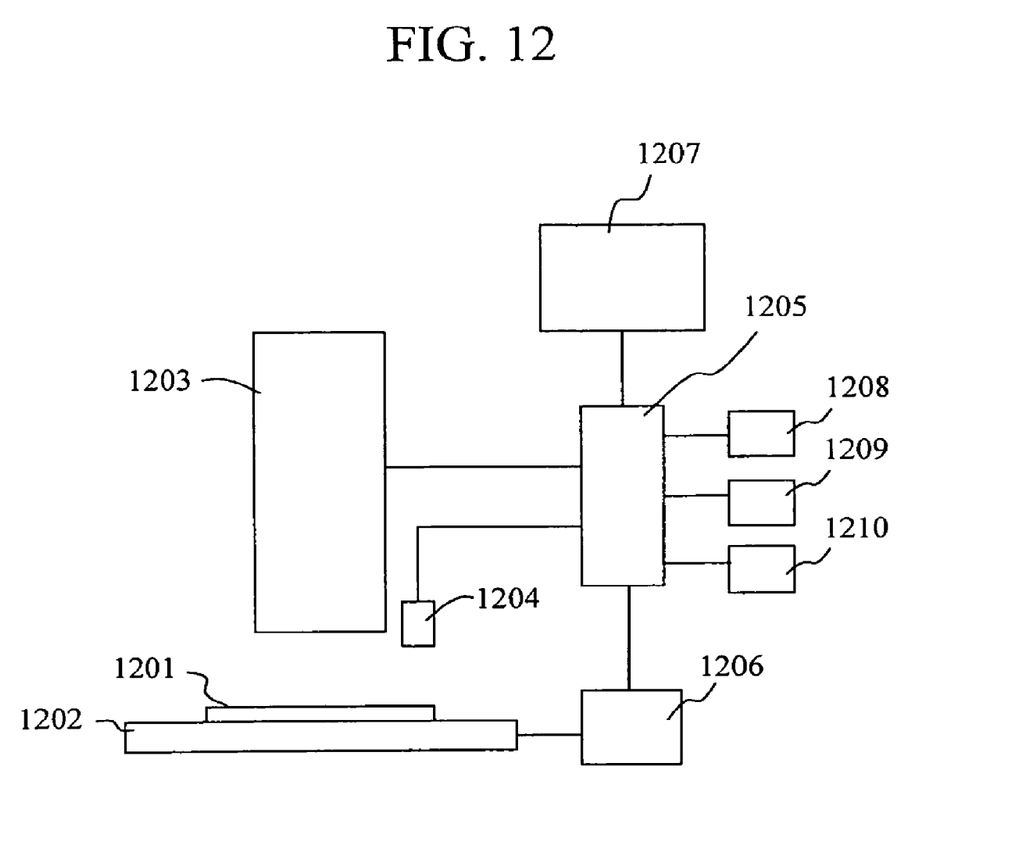
FIG. 12 shows a schematic diagram of an SEM defect review tool.

FIG. 12 shows a schematic diagram of the SEM defect review tool according to the invention. The defect review tool includes a sample stage 1202 for retaining and moving a test subject 1201, an electron beam column 1203 for scanning the test subject by irradiating it with an electron beam, and a secondary electron detector 1204 for detecting secondary electrons emitted by the test subject upon electron beam irradiation. The sample stage 1201 is driven to a desired stage coordinates position by a stage drive unit 1206, which is controlled by a control unit 1205. An electron beam image of the test subject, which is obtained by capturing a signal from the secondary electron detector 1204 in synchronism with the electron bean scan, is displayed on the display unit 1207. The defect information from the wafer inspection tool and the data handling tool is fed to the tool via a data input unit 1208. The display unit 1207 displays not only the defect image of the test subject, but also the screen 30 shown in FIG. 5, the operation screen shown in FIG. 7, and the windows shown in FIGS. 8-11 as needed. The scrolling operation on the screen shown in FIG. 5, and the operation of the defect selection button 48 for the selection of a defect to be displayed or the like, are carried out using an input device 1209, such as a keyboard or a mouse. The memory 1210 stores a table defining the relationship between a range of maximum gray level difference (Max GL_Diff) and the frame addition number, and a table defining the relationship between a defect size range and magnification. The control unit 1205 processes data that is input or performs image processing as well as controls the stage drive unit 1206, the electron beam column 1203, and the display unit 1207. Alternatively, the control unit 1205 may also provide the function of the data handling tool shown in FIGS. 1 and 2.

While the foregoing description has been made with reference to an SEM defect review tool, the structure of the SEM defect review tool shown in FIG. 12 will basically remain the same in the case of an optical defect review tool, with the only difference being that the electron beam column and the detector would be replaced with an optical microscope column and an imaging device, respectively.

What is claimed is:

1. A defect data processing method comprising the steps of:
   acquiring from a wafer inspection tool a plurality of pieces of defect information of each of defects obtained through a plurality of inspections on a test subject by the wafer inspection tool;
   identifying, from said plurality of pieces of defect information, defect information that is associated with the same defect based on coordinate information of said defects included in said plurality of pieces of defect information along with attribute information comprising an absolute value of the brightness of a defect part obtained from a subtract image between an image of a location that is determined as being defective and an image of a reference part thereof;
   outputting defect information concerning a defect to be reviewed to a defect review apparatus that uses a scanning electron microscope; and
   acquiring a defect image of a predetermined frame integration number corresponding to an absolute value of the brightness of said defect part of said defect to be reviewed in said defect review apparatus based on a table that describes a relationship between the absolute value of the brightness of said defects and the frame integration number of an image to be acquired by said scanning electron microscope.

2. The defect data processing method according to claim 1, wherein said plurality of inspections are performed by respectively varying inspection conditions.

3. The defect data processing method according to claim 1, wherein:
   said attribute information of said defect information also comprises size information of said defects, and
   in said step of acquiring said defect image, said defect image of said predetermined frame integration number is acquired at said defect review apparatus at a predetermined magnification corresponding to said size information of said defect to be reviewed based on a table that describes a relationship between the size of said defects and the magnification of said image to be acquired by the scanning electron microscope.

4. The defect data processing method according to claim 1, wherein said relationship in said table between the absolute value of the brightness of said defects and the frame integration number of said image to be acquired by said scanning electron microscope is displayed through a graph.

5. A defect review apparatus comprising:
   an input unit for accepting entry of defect information of a defect to be reviewed;
   a sample stage that is movable while carrying a test subject;
   an image acquiring unit for acquiring a scanning electron microscope image of said test subject;
   a control unit for controlling said sample stage and said image acquiring unit; and
   a table that describes the relationship between the absolute value of the brightness of a defect part and the frame integration number of the scanning electron microscope image acquired at said image acquiring unit,
   wherein said control unit:
   moves said sample stage in correspondence with coordinate information of said defect that is included in said defect information of said defect to be reviewed entered through said input unit along with attribute information comprising said absolute value of the brightness of said defect part obtained from a subtract image between an image of a location that is determined as being defective and an image of a reference part thereof;
   determines a predetermined frame integration number corresponding to said absolute value of the brightness of said defect part of said defect to be reviewed by referring to said table; and
   acquires a scanning electron microscope image of said defect to be reviewed while setting said image acquiring unit to said determined frame integration number.

6. The defect review apparatus according to claim 5, further comprising a table that describes a relationship between the size of a defect and the magnification of said scanning electron microscope image to be acquired at said image acquiring unit, wherein:
   said attribute information included in said defect information of said defect to be reviewed entered through said input unit also comprises size information of said defect, and
   said control unit acquires said scanning electron microscope image of said defect to be reviewed of said predetermined frame integration number at a predetermined magnification corresponding to said size information of said defect included in said attribute information by referring to the table that describes the relationship between size of defects and magnification.

7. The defect review apparatus according to claim 5, wherein said relationship in said table between the absolute value of the brightness of said defect and the frame integration number of said scanning electron microscope image to be acquired by said image acquiring unit is displayed through a graph.

8. A defect review apparatus comprising:
   an input unit for accepting entry of defect information of each of a plurality of defects obtained through a plurality of inspections of a test subject by a wafer inspection tool;
   a sample stage that is movable while carrying said test subject;
   an image acquiring unit for acquiring a scanning electron microscope image of said test subject;
   a control unit for controlling said sample stage and said image acquiring unit;
   a table that describes a relationship between the absolute value of the brightness of said defects and the frame integration number of said scanning electron microscope image to be acquired at said image acquiring unit; and
   a display unit for displaying defect information of a defect entered through said input unit and accepting an entry regarding the selection of a defect to be reviewed,
   wherein said control unit:
   identifies, from a plurality of pieces of defect information entered through said input unit, defect information that is associated with the same defect based on coordinate information of said defects included, along with attribute information comprising an absolute value of the brightness of a defect part obtained from a subtract image between an image of a location that is determined as being defective and an image of a reference part thereof, in said plurality of pieces of defect information entered through said input unit;
   causes said defect information that is associated with the same defect to be displayed on said display unit at once;
   moves said sample stage in correspondence with coordinate information in said defect information of said defect to be reviewed selected on said display unit;
   determines a predetermined frame integration number corresponding to said absolute value of the brightness of said defect part in said defect information of said defect to be reviewed by referring to said table; and acquires a scanning electron microscope image of said defect to be reviewed while setting said image acquiring unit to said determined frame integration number.

9. The defect review apparatus according to claim 8, further comprising a table that describes a relationship between the size of said defects and the magnification of said scanning electron microscope image to be acquired at said image acquiring unit, wherein:
  said attribute information included in said defect information of said defect entered through said input unit also comprises size information of said defect, and
  said control unit acquires said scanning electron microscope image of said defect to be reviewed of said predetermined frame integration number at a predetermined magnification corresponding to said size information of said defect included in said attribute information of said defect by referring to the table that describes the relationship between size of defects and magnification.

10. The defect review apparatus according to claim 8, wherein said relationship in said table between the absolute value of the brightness of said defects and the frame integration number of said scanning electron microscope image to be acquired at said image acquiring unit is displayed through a graph.

* * * * *